(12) United States Patent
Wudyka (10) Patent No.: US 8,167,869 B2
(45) Date of Patent: May 1, 2012

(54) WOUND THERAPY SYSTEM WITH PROPORTIONAL VALVE MECHANISM

(75) Inventor: Scott Wudyka, Marlborough, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 457 days.

(21) Appl. No.: 12/368,388

(22) Filed: Feb. 10, 2009

(65) Prior Publication Data

US 2010/0204663 A1   Aug. 12, 2010

(51) Int. Cl.
*A61M 27/00* (2006.01)
*A61M 1/00* (2006.01)

(52) U.S. Cl. ............................. 604/543; 604/35; 604/313

(58) Field of Classification Search .................. 604/35, 604/118–120, 313, 541, 543
See application file for complete search history.

(56) References Cited

U.S. PATENT DOCUMENTS

| | | | |
|---|---|---|---|
| 3,347,235 A * | 10/1967 | Hunnicutt | ..................... 604/120 |
| 3,367,332 A | 2/1968 | Groves | |
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,266,545 A | 5/1981 | Moss | |
| 4,382,441 A | 5/1983 | Svedman | |
| 4,524,064 A | 6/1985 | Nambu | |
| 4,743,232 A | 5/1988 | Kruger | |
| 4,885,001 A * | 12/1989 | Leppert | ........................ 604/6.11 |
| 4,888,003 A * | 12/1989 | Johnson et al. | ................ 604/319 |
| 4,969,880 A | 11/1990 | Zamierowski | |
| 4,990,137 A | 2/1991 | Graham | |
| 4,997,438 A | 3/1991 | Nipper | |
| 5,002,528 A * | 3/1991 | Palestrant | ........................ 604/28 |
| 5,032,260 A * | 7/1991 | Alzner | ........................... 210/137 |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,141,503 A | 8/1992 | Sewell, Jr. | |

(Continued)

FOREIGN PATENT DOCUMENTS

DE   41 11 122 A1   4/1993

(Continued)

OTHER PUBLICATIONS

Meyer, M.D., et al., "In Surgery, Medicine and the Specialties A Manual of its Practical Application", Bier's Hyperemic Treatment, Second Revised Edition, W.B. Saunders Company, 1909.

(Continued)

*Primary Examiner* — Melanie Hand
*Assistant Examiner* — Paula Craig
(74) *Attorney, Agent, or Firm* — Elias Domingo, Esq.

(57) ABSTRACT

A system for subatmospheric pressure therapy in connection with healing a wound includes a wound dressing adapted for positioning relative to a wound bed of a subject to apply a subatmospheric pressure to the wound and a subatmospheric pressure mechanism. The subatmospheric pressure mechanism may be portable and adapted to be carried or worn by the subject.

9 Claims, 3 Drawing Sheets

U.S. PATENT DOCUMENTS

| | | |
|---|---|---|
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,503,143 A * | 4/1996 | Marion et al. ........... 128/202.12 |
| 5,516,119 A * | 5/1996 | Trackwell et al. ........... 277/409 |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,840,049 A | 11/1998 | Tumey et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,083,195 A * | 7/2000 | Perkins et al. ................... 604/30 |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,794,450 B2 * | 9/2010 | Blott et al. ..................... 604/543 |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2002/0198503 A1 | 12/2002 | Risk, Jr. et al. |
| 2003/0093041 A1 | 5/2003 | Risk, Jr. et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0122434 A1 | 6/2004 | Argenta et al. |
| 2004/0193218 A1 | 9/2004 | Butler |
| 2004/0241213 A1 | 12/2004 | Bray |
| 2004/0243073 A1 | 12/2004 | Lockwood et al. |
| 2005/0004534 A1 * | 1/2005 | Lockwood et al. ........... 604/304 |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2007/0014837 A1 | 1/2007 | Johnson et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0066946 A1 | 3/2007 | Haggstrom et al. |

| | | | |
|---|---|---|---|
| 2007/0078366 | A1 | 4/2007 | Haggstrom et al. |
| 2007/0167927 | A1 | 7/2007 | Hunt et al. |
| 2007/0179460 | A1 | 8/2007 | Adahan |
| 2007/0276309 | A1 | 11/2007 | Xu et al. |

FOREIGN PATENT DOCUMENTS

| | | |
|---|---|---|
| DE | 295 04 378 U1 | 10/1995 |
| DE | 43 06 478 AL | 12/2008 |
| EP | 0 020 662 B1 | 7/1984 |
| EP | 0 358 302 | 3/1990 |
| EP | 0 853 950 B1 | 10/2002 |
| GB | 1 549 756 | 3/1977 |
| GB | 2 195 255 A | 4/1988 |
| GB | 2 235 877 A | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1991 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

Jeter, Katherine F., et al., "Managing Draining Wounds and Fistulae: New and Established Methods", Chronic Wound Care, 1990, pp. 240-246.
Chariker, M. E. et al. (eds), "Effective Management of Incisional and Cutaneous Fistulae with Closed Suction Wound Drainage," Contemporary Surgery, vol. 34, Jun. 1989, pp. 59-63.
B.M. Kostiuchenok, et al., "The Vacuum Effect in the Surgical Treatment of Purulent Wounds," Russian Journal: Vestnik Khirugii, Sep. 1986 (18-21).
Y.N. Usupov, et al., "Active Wound Drainage," Russian Journal: Vestnik Khirugii, Apr. 1987 (42-45).
Yu A. Davydov, et al., "Concepts for Clinical Biological Management of the Wound Process in the Treatment of Purulent Wounds Using Vacuum Therapy," Vestnik Khirugii, Feb. 1991, 132-135).
N.A. Bagautdinov (Kazan), "Variant of External Vacuum Aspiration in the Treatment of Purulent Diseases of Soft Tissues," UDC 616-002.36 (94-96).
Chardack, et al., "Experimental studies on Synthetic Substitutes for Skin and Their Use in the Treatment of Burns," vol. 155, No. 1 (128-136).
Gorica Zivadinovic, et al., "Vacuum Therapy in the Treatment of Peripheral Blood Vessels," Conference Papers of the 5th Timok Medical Days, Majdanpek, 1986 (161-164).
Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).
W. Fleischmann, et al., Vacuum Sealing: Indication, Technique and Results, Emr J Orthop Surg Tramatol (1995) 5:37-40.
Sherry Stoll, "Energetic Remedies—Cupping: Healing Within a Vacuum," https://www.suite101.com/article.cfm/energetic/remedies/74531, Apr. 13, 2005.
Mulder, G.D, et al., "Clinicians' Pocket Guide to Chronic Wound Repair," Wound Healing Publications Second Edition, 1991.
Yu A. Davydov, et al., "Vacuum Therapy in the Treatment of Purulent Lactation Mastitis," Russian Journal: Vesnik Khirurgii, Sep. 1986 (66-70).
Yu A. Davydov, et al., "Bacteriological and Cytological Assessment of Vacuum Therapy of Purulent Wounds", Vestnik Khirurgii, Oct. 1988 (48-52).
W. Fleischmann, "Vacuum Sealing for Treatment of Problematical Wounds", University Surgical Clinic and Polyclinic—Accident Surgery Department, WundForum Spezial—IHW 94.
Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Björn, et al., "Irrigation Treatment in Split-thickness Skin Grafting of Intractable Leg Ulcers," Scand J Plast Reconstr Surg 19: 211-213, 1985.
Paul Svedman, et al., "Staphylococcal Wound Infection in the Pig: Part I. Course," Annals of Plastic Surgery, vol. 23, No. 3, Sep. 1989 (212-218).
Paul Svedman, "A Dressing Allowing Continuous Treatment of a Biosurface," IRCS Medical Science: Biomedical Technology; Clinical Medicine; Surgery and Transplantation, 7, 221 (1979).
Paul Svedman, "Irrigation Treatment of Leg Ulcers," The Lancet, Sep. 3, 1983 (532-534).
H. Teder, et al., "Continuous Wound Irrigation in the Pig," Journal of Investigative Surgery, vol. 3 (399-407).
P. Svedman, "A Dressing System Providing Fluid Supply and Suction Drainage Used for Continuous or Intermittent Irrigation," Annals of Plastic Surgery, vol. 17, No. 2, Aug. 1986 (125-133).
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.
International Search Report from corresponding Application No. PCT/US2010/021148 mailed Mar. 22, 2010.
US 6,216,701, 04/2001, Heaton et al. (withdrawn)
US 7,186,244, 03/2007, Hunt et al. (withdrawn)

* cited by examiner

WOUND THERAPY SYSTEM WITH PROPORTIONAL VALVE MECHANISM

BACKGROUND

1. Technical Field

The present disclosure relates to treating an open wound by applying negative pressure to the wound, and, more particularly, to a portable wound therapy system including a valve mechanism that allows the portable wound therapy system to operate continuously.

2. Discussion of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e., an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy, also known as suction or vacuum therapy, has been used in treating and healing wounds. Treating an open wound by applying negative pressure, e.g., reduced or subatmospheric pressure, to a localized reservoir over a wound has been found to assist in closing the wound by increasing blood circulation at the wound area, stimulating the formation of granulation tissue, and promoting the migration of healthy tissue over the wound. Negative pressure therapy may also inhibit bacterial growth by drawing fluids from the wound such as exudate, which may tend to harbor bacteria. This technique has proven effective for treating a variety of wound conditions, including chronic or healing-resistant wounds and ulcers, and is also used for other purposes such as post-operative wound care.

Generally, negative pressure therapy provides for a wound covering to be positioned over the wound to facilitate suction at the wound area. A conduit is introduced through the wound covering to provide fluid communication to an external vacuum source, such as a hospital vacuum system or a portable vacuum pump. Atmospheric gas, wound exudate, or other fluids may thus be drawn from the reservoir through the fluid conduit to stimulate healing of the wound. Exudate drawn from the reservoir may be deposited into a collection canister.

Often, a negative pressure wound therapy device is carried or worn by the patient, including in public. Operation of the device may make the device intrusive and non-discrete. For example, the vacuum source may intermittently start or stop during operation to achieve and/or maintain a specific vacuum level at the wound. The intermittent starts and stops cause the therapy device to be intrusive on the patient and the resulting noise makes the therapy device non-discrete in public. As a result, the patient may become dissatisfied or non-compliant with wearing the therapy device. A reduction in negative pressure therapy duration may inhibit wound healing or cause the wound to become infected. One way to reduce the intrusive nature of the therapy device is to configure the therapy device to run continuously such that intermittent starts or stops and noise are eliminated.

SUMMARY

The present disclosure relates to a system for subatmospheric pressure therapy in connection with healing a surgical or chronic wound including a wound dressing, which is adapted for positioning relative to a wound bed of a subject to apply a subatmospheric pressure to the wound, and a subatmospheric pressure mechanism. The subatmospheric pressure mechanism may be portable and adapted to be carried or worn by the subject. The subatmospheric pressure mechanism includes a housing, a vacuum source disposed in the housing and having an inlet port and an outlet port, and a collection canister. The collection canister is in fluid communication with the vacuum source via the inlet port and with the wound dressing for collecting exudate removed from the wound bed under influence of the vacuum source.

The subatmospheric pressure mechanism also includes a valve mechanism disposed relative to the vacuum source between the inlet and outlet ports. The valve mechanism is adapted to move between an open position where the vacuum source is capable of drawing a vacuum in the collection canister, a proportional position where the outlet port of the vacuum source is placed in fluid communication with the inlet port of the vacuum source, and a closed position where fluid communication between the inlet port of vacuum source and the wound dressing is interrupted.

BRIEF DESCRIPTION OF THE DRAWINGS

Objects and features of the presently disclosed wound therapy system will become apparent to those of ordinary skill in the art when descriptions of various embodiments thereof are read with reference to the accompanying drawings, of which.

DETAILED DESCRIPTION

Hereinafter, embodiments of the presently disclosed wound therapy system will be described with reference to the accompanying drawings. Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both.

The wound therapy system of the present disclosure promotes healing of a wound via the use of a wound dressing and a portable subatmospheric pressure mechanism. Generally, the portable subatmospheric pressure mechanism applies subatmospheric pressure to the wound to effectively remove wound fluids or exudate captured within the boundary of the composite wound dressing, and to increase blood flow to the wound bed and enhance cellular stimulation of epithelial and subcutaneous tissue. The wound therapy system may be entirely portable, i.e., it may be worn or carried by the subject such that the subject may be completely ambulatory during the therapy period. The wound therapy system including the subatmospheric pressure mechanism and components thereof may be entirely reusable or may be entirely disposable after a predetermined period of use or may be individually disposable whereby some of the components are reused for a subsequent therapy application.

The wound therapy system of the present disclosure promotes healing of a wound in conjunction with negative pressure therapy. The system may incorporate a variety of wound dressings, subatmospheric pressure sources and pumps, and collection canisters.

Figure 1:
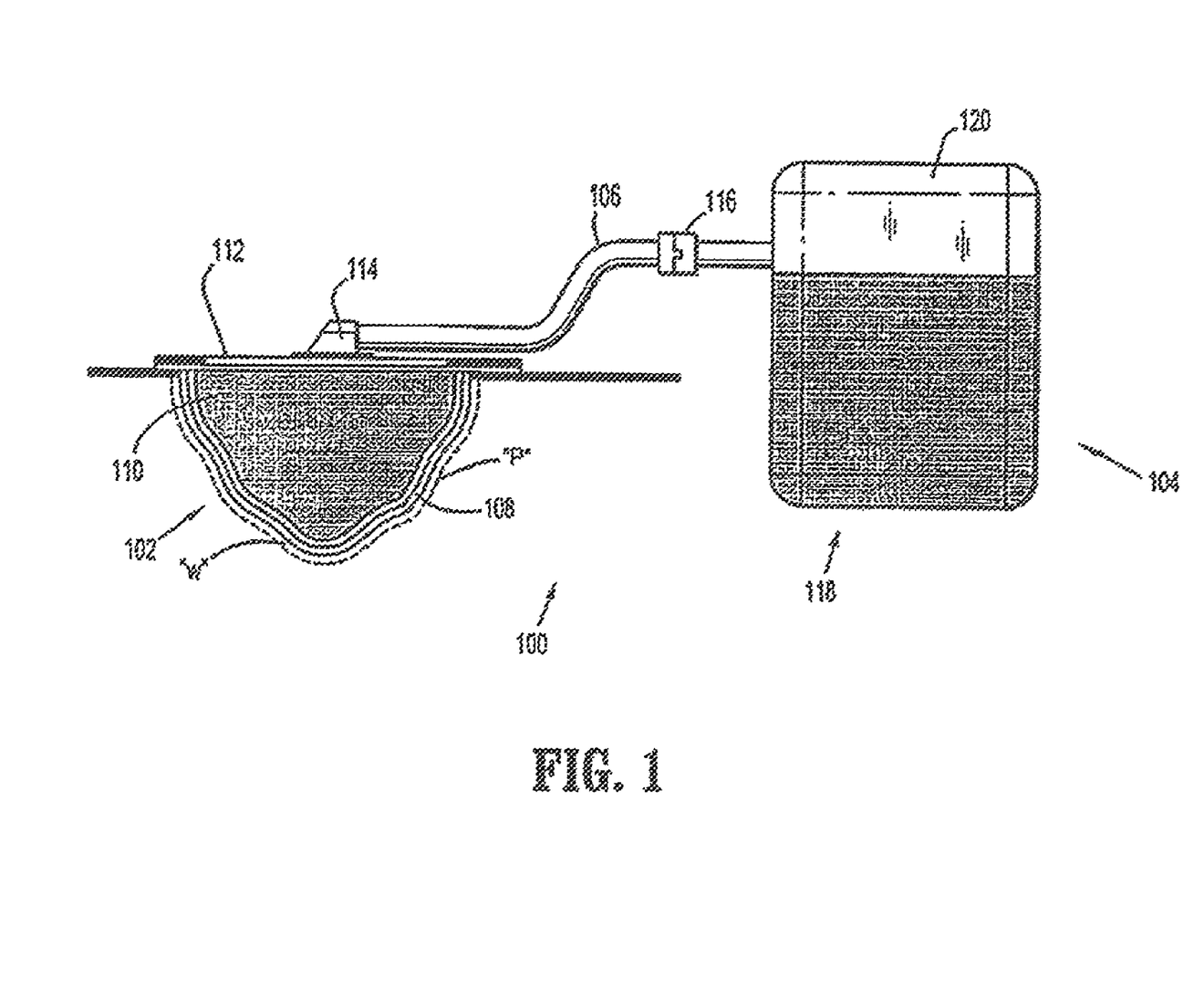
FIG. 1 is a view in partial cross-section of the portable wound therapy system of the present disclosure illustrating the wound dressing and the subatmospheric pressure mechanism.

Referring initially to FIG. 1, a wound therapy system according to an embodiment of the present disclosure is depicted generally as 100 for use on a wound bed "w". Wound therapy system 100 includes a composite wound dressing 102 and a subatmospheric pressure mechanism 104 in fluid communication with the wound dressing 102 via a conduit 106.

Wound dressing 102 may include several components, namely, a wound contact layer or member 108, a wound packing member or filler 110 supported by the contact member 108 and an outer member or wound covering 112. Wound contact member 108 is intended for placement within the wound bed "w" and adapted to substantially conform to the topography of a wound bed "w". For example, the wound contact member 108 may be relatively non-supportive or flexible to substantially conform to the topography of a wound bed "w". Wound contact member 108 is substantially porous or perforated and may be formed from perforated film material. The porous characteristic of the wound contact member 108 permits exudate to pass from the wound bed "w" through the wound contact member 108. The passage of wound exudate through the wound contact member 108 may be unidirectional such that wound exudate does not flow back to the wound bed "w". Unidirectional flow may be encouraged by directional apertures, e.g., apertures positioned at peaks of undulations or cone-shaped formations protruding from the wound contact member 108. Unidirectional flow may also be encouraged by laminating the wound contact member 108 with materials having absorption properties differing from those of the wound contact member 108, or by selection of materials that promote directional flow. A variety of materials may be used for the wound contact member 108. Wound contact member 108 selection may depend on various factors such as the patient's condition, the condition of the periwound skin, the amount of exudate and/or the condition of the wound bed "w". A non-adherent material may be selected for forming the wound contact member 108 such that the contact member 108 does not tend to cling to the wound bed "w" or surrounding material when it is removed. One example of a material that may be suitable for use as a wound contact member 108 is commercially available under the trademark XEROFORM® offered by Tyco Healthcare Group LP (d/b/a Covidien). Another example of a material that may be suitable for use as the contact member 108 is the commercially available CURITY® non-adherent dressing offered by Tyco Healthcare Group LP (d/b/a Covidien).

Wound packing member 110 of the wound dressing 102 is intended to transfer wound fluids and exudate. Wound packing member 110 is conformable to assume the shape of any wound bed "w" and may be packed up to any level, e.g., up to the level of healthy skin or to overfill the wound such that wound packing member 110 protrudes over healthy skin. Wound packing member 110 may be treated with agents such as polyhexamethylene biguanide (PHMB) to decrease the incidence of infection and/or other medicaments to promote wound healing. A variety of materials may be used for the wound packing member 110. An example of a material that may be suitable for use as the wound packing material 110 is the antimicrobial dressing commercially available under the trademark KERLIX® AMD® offered by Tyco Healthcare Group LP (d/b/a Covidien).

Outer member or wound covering 112 encompasses the perimeter of the wound dressing 102 to surround wound bed "w" and to provide a substantially fluid-tight seal around the perimeter "p" of the wound bed "w". For instance, the sealing mechanism may be any suitable adhesive bonded to the perimeter of wound covering 112. For example, the wound dressing 102 may include a substantially continuous band of a biocompatible adhesive at the periphery of the wound covering 112. One example of a material that may be used as an adhesive dressing is commercially available under the trademark CURAFORM ISLAND® offered by Tyco Healthcare Group LP (d/b/a Covidien). Wound covering 112 may act as both a microbial barrier and a fluid barrier to prevent contaminants from entering the wound bed "w" and to help maintain the integrity thereof.

Wound covering 112 may be a flexible material, e.g., resilient or elastomeric, that seals the top of wound dressing 102 to prevent passage of liquids, fluids, or contamination to and from the wound dressing 102. Wound covering 112 may be formed from a moisture vapor permeable membrane, e.g., to promote the exchange of oxygen moisture between the wound bed "w" and the atmosphere. An example of a membrane that may provide a suitable moisture vapor transmission rate is a transparent membrane commercially available under the trademark POLYSKIN® II offered by Tyco Healthcare Group LP (d/b/a Covidien). A transparent membrane may help to permit a visual assessment of wound conditions to be made without requiring removal of the wound covering 112. Wound covering 112 may be formed of an impermeable membrane. Wound covering 112 may be formed of a substantially rigid membrane.

Wound covering 112 may include a port or connector 114 in fluid communication with the interior of the wound dressing 102 to facilitate connection of the wound dressing 102 to the conduit or tubing 106. Conduit 106 defines at least part of the fluid flow path leading through wound therapy system 100. Connector 114 may be configured as a rigid or flexible, low-profile component, and may be adapted to receive the conduit 106 in a releasable and fluid tight manner. A hollow interior of the connector 114 provides fluid communication between the conduit 106 and the interior of the wound dressing 102. Connector 114 may have a valve shown schematically as reference numeral 116 built therein or in line with the conduit 106, e.g., such as a one-way valve to permit exudate to flow in one direction only, i.e., away from the wound dressing 102 toward the subatmospheric pressure mechanism 104. Connector 114 may be provided as a pre-affixed component of the wound dressing 102, as a component of the conduit 106 or entirely separate and connected thereto by conventional means. Alternatively, connector 114 may be eliminated if other provisions are made for providing fluid communication between the wound dressing 102 and the conduit 106.

Conduit 106 extends from the subatmospheric pressure mechanism 104 to provide fluid communication between the interior of the wound dressing 102 and the subatmospheric pressure mechanism 104. Any suitable conduit may be used for the conduit 106, including conduit fabricated from flexible elastomeric or polymeric materials. Conduit 106 may connect to subatmospheric pressure mechanism 104 or other system components by conventional air-tight means, such as, for example, friction fit, bayonet coupling, or barbed connectors. The conduit connections may be made permanent. Alternately, a quick-disconnect or other releasable connection means may be used to provide some adjustment flexibility to the apparatus 100.

Figure 2:
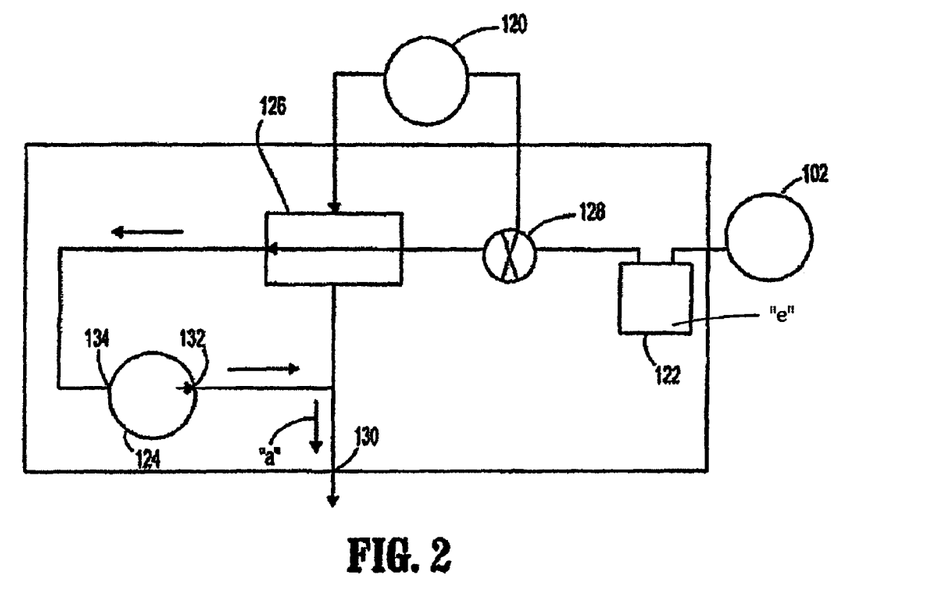
FIG. 2 is a schematic view of the subatmospheric pressure mechanism of the portable wound therapy system illustrated in FIG. 1 shown with the proportional valve in an open position.
Figure 3:
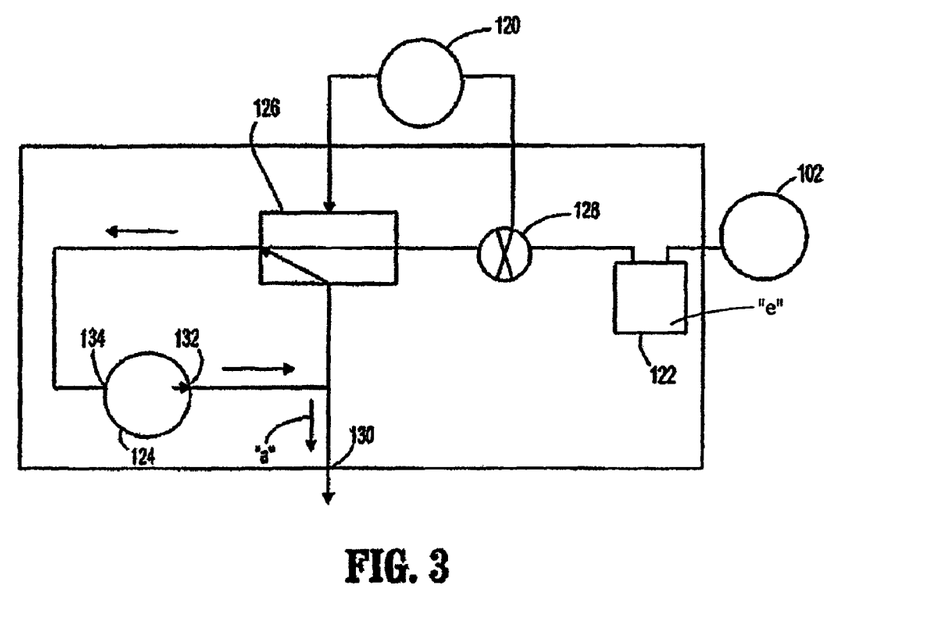
FIG. 3 is a schematic view of the subatmospheric pressure mechanism of the portable wound therapy system illustrated in FIG. 1 shown with the proportional valve in a proportional position.
Figure 4:
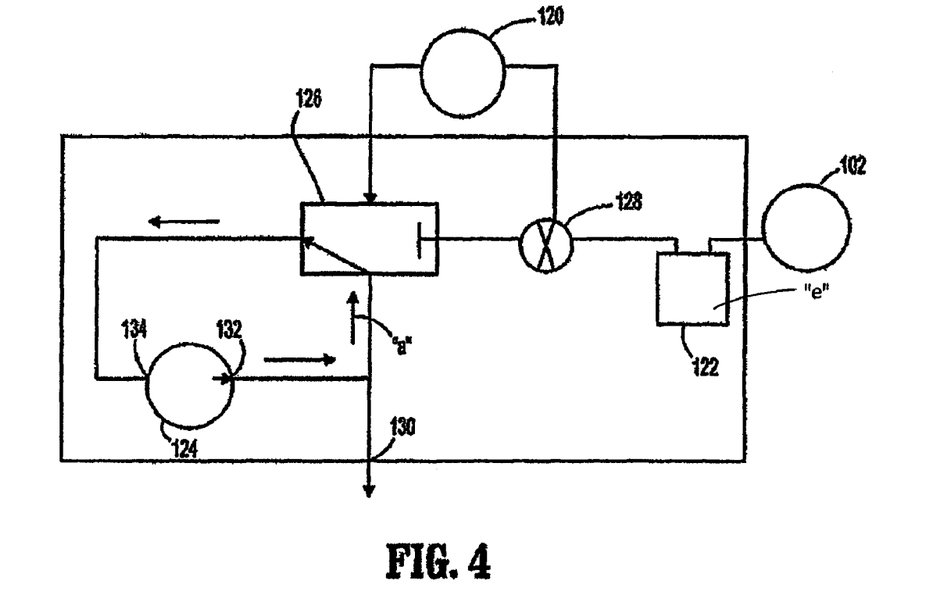
FIG. 4 is a schematic view of the subatmospheric pressure mechanism of the portable wound therapy system illustrated in FIG. 1 shown with the proportional valve in a closed position.

Referring now to FIGS. 2-4, in conjunction with FIG. 1, subatmospheric pressure mechanism 104 will be discussed. Subatmospheric pressure mechanism 104 includes a housing 118, a control unit 120 (also shown schematically in FIG. 1), a pressure transducer 128, a vacuum source or pump 124, a valve mechanism 126, and a collection canister 122. Housing 118 may be any suitable rigid member adapted for donning by the subject. Control unit 120 may incorporate a suitable power source (not shown) disposed within the housing or separately mounted thereto for activating the vacuum source or pump 124. A suitable power source may be, for example, alkaline batteries, wet cell batteries, dry cell batteries, nickel cadmium batteries, solar generated means, lithium batteries, NiMH batteries (nickel metal hydride) each of which may be of the disposable or rechargeable variety. Vacuum source or pump 124 includes an inlet port 134 fluidly coupled to the wound dressing 102 and an outlet port 132 suitably adapted to expel exhaust air from the vacuum source 124. Vacuum source or pump 124 generates or otherwise provides negative pressure to wound therapy system 100. Vacuum source or pump 124 may be a pump of the diaphragmatic, peristaltic or bellows type or the like, in which the moving part(s) draw exudate out of the wound bed "w" into the wound dressing 102 by creating areas or zones of decreased pressure e.g., vacuum zones with the wound dressing 102. This area of decreased pressure preferably communicates with the wound bed "w" to facilitate removal of the fluids therefrom and into the absorbent or non-absorbent packing member 110.

Vacuum source or pump 124 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg and about 125 mmHg, or between about 30 mmHg and 80 mmHg. Vacuum source or pump 124 is actuated by a suitable actuator (not shown) which may be any means known by those skilled in the art, including, for example, AC motors, DC motors, voice coil actuators, solenoids, etc, and may be incorporated within pump 124.

Housing 118 further includes an exhaust port 130 configured to vent exhaust air from vacuum source or pump 124. Exhaust port 130 extends from the housing 118 and may be directly connected to vacuum source outlet port 132. It is also envisioned that the exhaust port 130 may exhaust air from within the housing 118 rather than directly from the vacuum source 124. Exhaust port 130 may include a suitable filter (e.g., a bacterial filter) to prevent emission of bacteria from the housing 118.

Collection canister 122 collects exudate "e" removed from the wound bed "w" during therapy through the conduit, or tubing, 106. Collection canister 122 is associated with the housing 118 and may be incorporated within the housing 118 or releasably connected to the housing 118 by conventional means. Housing 118 and the collection canister 122 of the subatmospheric pressure mechanism 104 may be releasably coupled. Mechanisms for selective coupling and decoupling of the housing 118 and the collection canister 122 include fasteners, latches, clips, straps, bayonet mounts, magnetic couplings, and other devices.

Collection canister 122 may comprise any container suitable for containing wound fluids and is substantially rigid defining an internal chamber in fluid communication with the tubing 106. Collection canister 122 may contain an absorbent material to consolidate or contain the wound drainage or debris. In embodiments, at least a portion of the collection canister 122 may be transparent or semi-transparent, e.g., to permit a visual assessment of the wound exudate to assist in evaluating the color, quality, and/or quantity of wound exudate. A transparent or semi-transparent canister may assist in determining the remaining capacity or open volume of the canister and/or may assist in determining whether to replace the collection canister 122. In the alternative, collection canister 122 may be relatively flexible.

Vacuum pressure transducer 128 provides feedback to control unit 120. More specifically, pressure transducer 128 is in fluid communication with collection canister 122 to detect the vacuum level at the collection canister. In one embodiment, the pressure transducer 128 generates an electrical signal that varies as a function of vacuum level at the collection canister 122, which is communicated to the control unit 120. Logic associated with the pressure transducer 128 and the pump 124 may reduce the speed of the pump 124 or stop operation of the pump 124 in response to the vacuum level detected by the pressure transducer 128. Audible indicatory means may also be incorporated or associated with the computer logic to notify the user of a condition. Control unit 120, in response to feedback from the pressure transducer 128, controls the valve mechanism 126 to adjust vacuum pressure on the wound "w". More specifically, the valve mechanism 126 is controllable by the control unit 120 to selectively allow varying amounts of exhaust air from the pump outlet port 132 to circulate back into the pump inlet port 134, thereby allowing the pump 124 to operate continuously, as will be discussed in further detail below.

With specific reference to FIG. 2, subatmospheric pressure mechanism 104 is shown operating in a setpoint mode. In the setpoint mode, the pump 124 operates at a relatively fast speed to ramp up negative pressure at the collection canister 122 to a desired vacuum level or setpoint to create a reduced pressure state within wound dressing 102. The setpoint may be, for example, a desired pressure set by the user. In the setpoint mode, valve mechanism 126 assumes the open position depicted in FIG. 2 to place wound dressing 102 in direct pneumatic communication with the inlet port 134 of pump 124. Exhaust air from the pump outlet port 132 is vented through the exhaust port 130.

Referring specifically now to FIG. 3, subatmospheric pressure mechanism 104 is shown operating in a proportional mode wherein the desired vacuum level or setpoint has been achieved or a level substantially equivalent to the setpoint has been achieved. In the proportional mode, the pump 124 operates at a relatively slow speed and the valve mechanism 126 assumes the proportional position depicted in FIG. 3. In the proportional position, the valve mechanism 126 allows exhaust air from the pump output 132 to circulate back into the pump inlet port 134. The air pressure provided by the air flow from the pump outlet port 134 at the pump inlet port 134 enables the pump 124 to operate continuously at a relatively slow speed without stalling. Further, the valve mechanism 126 creates a conduit for air flow from the wound "w" to the exhaust 130, thereby providing additional vacuum relief by venting air flow from the wound "w".

Referring now to FIG. 4, subatmospheric pressure mechanism 104 is shown operating in an over-vacuum mode wherein a higher than desired vacuum level at the collection canister 122 is detected by the pressure transducer 128. Conditions such as leaks at the wound site, clogs, container tips may induce a higher than desired vacuum level measured by the pressure transducer 128. In this scenario, the valve mechanism 126 assumes the closed position depicted in FIG. 4 to close off fluid communication between the pump 124 and the wound "w". Air "a" is only permitted to circulate from the pump outlet port 132 to the pump inlet port 134, thereby creating an air loop wherein air flow from the outlet port 132 creates continuous air pressure at the inlet port 134. The air flow at the inlet port 134 allows the pump 124 to operate continuously while vacuum pressure at the wound bed "w" is relieved. In this way, stopping operation of the pump 124 while in the over-vacuum mode is not necessary to relieve the vacuum level at the wound bed "w". In the over-vacuum mode, a vacuum change (e.g., drop in vacuum) will alert the subject of the condition. The vacuum change may be identified or recognized by the user through increased noise or churning of the vacuum pump 124. In the alternative, the pressure transducer 128 may be in communication with the collection canister 122 to detect changes in pressure. Control unit 120 and/or logic associated with the pressure transducer 128 and the pump 124 may reduce the speed of the pump 124 or stop operation of the pump 124 in response to the vacuum level detected by the pressure transducer 128. Audible indicatory means may also be incorporated or associated with the computer logic to notify the user of the condition.

Once vacuum pressure at the wound is sufficiently relieved, the subatmospheric pressure mechanism 104 operates in either the setpoint mode or the proportional mode, as described above.

In use, the wound dressing is placed adjacent the wound bed "w" and connected to the subatmospheric pressure mechanism 124 via the tubing 106, as illustrated in FIG. 1. Control unit 120 of subatmospheric pressure mechanism 104 maintains the valve mechanism 126 in the open position depicted in FIG. 2 during the set point mode to create a reduced pressure state within wound dressing 102. Vacuum source or pump 124 may be set at a specific set point whereby the pump 124 will begin to draw vacuum until it achieves the set point as detected, e.g., by the pressure transducer 128. As pumping progresses, exudate are collected and directed to collection canister 122. Once the set point vacuum level is achieved, control unit 120 maintains the valve mechanism 126 in the proportional position depicted in FIG. 3 during the proportional mode wherein the vacuum reading at the pump will stay at this level (e.g., vacuum equilibrium) until the set point is changed, the pump is turned off, or there is a condition that causes a higher than desired vacuum level (e.g., a clog in the system) or an inability to continue to achieve the desired vacuum level (e.g., an air leak in the system). In the event of a higher than desired vacuum level measured by the pressure transducer 128 (e.g., due to a clog in the system, tilting of the collection canister 122 beyond a predetermined angle of orientation, e.g., relative to an upright position of the collection canister 122, or inversion of the collection canister 122), the subatmospheric pressure mechanism 104 operates in the over-vacuum mode and valve mechanism 126 will assume the position of FIG. 4 to close off fluid communication between the pump 124 and the wound "w" until the vacuum pressure at the wound "w" is sufficiently relieved.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A portable system for subatmospheric pressure therapy in connection with healing a wound, which comprises:
   a wound dressing dimensioned for positioning relative to a wound bed of a subject to apply a subatmospheric pressure to the wound;
   a subatmospheric pressure mechanism including:
     a housing;
     a vacuum source disposed in the housing and having an inlet port and an outlet port, the inlet port fluidly couplable to the wound dressing via a conduit;
     a collection canister in fluid communication with the inlet port and the wound dressing via the conduit for collecting exudate removed from the wound bed;
     a valve mechanism disposed relative to the vacuum source and fluidly coupled to the inlet and outlet ports via the conduit; and
     an exhaust port in fluid communication with the wound dressing via the valve mechanism and with the outlet port of the vacuum source, the exhaust port configured to vent an air flow from at least one of the vacuum source and the wound dressing;
     wherein the valve mechanism is adapted to move between an open position where the vacuum source is capable of drawing a vacuum in the collection canister through the inlet port via the conduit and an air flow from the outlet port is vented through the exhaust port, a proportional position where the outlet port is placed in fluid communication with the inlet port through the valve mechanism via the conduit such that an air flow exits from the outlet port and circulates through the valve mechanism and into the inlet port and an air flow from the wound dressing is vented through the exhaust port, and a closed position where an air flow from the outlet port circulates through the inlet port and fluid communication between the inlet port and the wound dressing is interrupted.

2. The portable system according to claim 1, wherein the valve mechanism is adapted to move to the closed position in response to one of a clog, an air leak at the wound dressing, a tilting of the collection canister beyond a predetermined angle of orientation, and an inversion of the collection canister.

3. The portable system according to claim 2, wherein the predetermined angle of orientation is relative to an upright position of the collection canister.

4. The portable system according to claim 1, the subatmospheric pressure mechanism further comprising a control unit in communication with a pressure transducer adapted to detect a vacuum level at the collection canister, the control unit adapted to move the valve mechanism between the open, proportional, and closed positions in response to the vacuum level detected by the pressure transducer.

5. The portable system according to claim 4, wherein the pressure transducer is adapted to generate an electrical signal which varies as a function of vacuum level at the collection canister.

6. The portable system according to claim 1, wherein the vacuum source is adapted to run continuously.

7. A method of healing a wound using subatmospheric pressure therapy, the steps comprising:
   positioning a wound dressing relative to a wound bed of a subject;
   applying subatmospheric pressure to the wound bed via a subatmospheric pressure mechanism, the subatmospheric pressure mechanism comprising:
     a housing;

a vacuum source disposed in the housing and having an inlet port and an outlet port, the inlet port fluidly coupled to the wound dressing via a conduit;

a collection canister in fluid communication with the inlet port and the wound dressing via the conduit for collecting exudate removed from the wound bed under influence of the vacuum source; and a valve mechanism disposed relative to the vacuum source and fluidly coupled to the inlet and outlet ports via the conduit;

venting an air flow from at least one of the vacuum source and the wound dressing via an exhaust port in fluid communication with the wound dressing via the valve mechanism and with the outlet port of the vacuum source, operating the vacuum source with the valve mechanism in an open position to vent an air flow from the outlet port through the exhaust port and achieve a reduced pressure state within the wound dressing at a desired vacuum level;

moving the valve mechanism to a proportional position upon achievement of the desired vacuum level to place the outlet port in fluid communication with the inlet port through the valve mechanism via the conduit; and moving the valve mechanism to a closed position to interrupt fluid communication between the inlet port and the wound dressing and relieve vacuum pressure at the wound dressing if a higher than desired vacuum level is achieved;

wherein the step of moving the valve mechanism to the proportional position further comprises circulating an air flow from the outlet port through the valve mechanism and into the inlet port and venting an air flow from the wound dressing through the exhaust port; and the step of moving the valve mechanism to the closed position further comprises circulating an air flow from the outlet port through the valve mechanism and into the inlet port to interrupt the influence of the vacuum source on the wound bed.

8. The method according to claim 7, further comprising the steps of:

detecting a vacuum level at the collection canister; and moving the valve mechanism between the open, proportional, and closed positions in response to the detected vacuum level.

9. The portable system according to claim 8, further comprising the step of:

generating an electrical signal that varies as a function of the detected vacuum level.

\* \* \* \* \*